(12) United States Patent
Neuneker et al.

(10) Patent No.: US 10,651,672 B2
(45) Date of Patent: May 12, 2020

(54) MOVABLE CHARGING COIL WITHIN WRISTBAND

(71) Applicant: HEWLETT-PACKARD DEVELOPMENT COMPANY, L.P., Houston, TX (US)

(72) Inventors: Jonathan Neuneker, Boise, ID (US); Paul Michael Carson, Boise, ID (US); Ian Christopher Shatto, Boise, ID (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/749,087

(22) PCT Filed: Jan. 13, 2016

(86) PCT No.: PCT/US2016/013142
§ 371 (c)(1),
(2) Date: Jan. 30, 2018

(87) PCT Pub. No.: WO2017/123212
PCT Pub. Date: Jul. 20, 2017

(65) Prior Publication Data
US 2018/0219401 A1    Aug. 2, 2018

(51) Int. Cl.
*H02J 7/00* (2006.01)
*H01F 27/42* (2006.01)
(Continued)

(52) U.S. Cl.
CPC ............. *H02J 7/025* (2013.01); *A61B 5/024* (2013.01); *A61B 5/681* (2013.01); *H02J 5/005* (2013.01);
(Continued)

(58) Field of Classification Search
USPC .......................................... 320/108; 307/104
See application file for complete search history.

(56) References Cited

U.S. PATENT DOCUMENTS

| | | | | |
|---|---|---|---|---|
| 6,101,842 A * | 8/2000 | Delacretaz | ............. | A44C 5/107 24/265 B |
| 2008/0122660 A1* | 5/2008 | Koganei | ................... | G06F 1/16 341/22 |

(Continued)

FOREIGN PATENT DOCUMENTS

| | | |
|---|---|---|
| CN | 103490487 A | 1/2014 |
| CN | 104113124 A | 10/2014 |

(Continued)

OTHER PUBLICATIONS

"Hidden Diagnostic Port on Apple Watch Can Be Used to Charge From Smart Straps"; applewatch news; http://www.smartwatch.me/t/hidden-diagnostic-port-on-apple-watch-can-be-used-to-charge-from-smart-straps/965; Downloaded Oct. 19, 2015.

*Primary Examiner* — Richard Isla
*Assistant Examiner* — Mohammed J Sharief
(74) *Attorney, Agent, or Firm* — Perry + Currier Inc.

(57) ABSTRACT

Example implementations relate to a movable charging coil within a wristband. For example, an apparatus includes a computing device and a wristband coupled to the computing device. The wristband includes a movable carriage that is movable within the wristband. The movable carriage has a charging coil to wirelessly receive power from a charging device when the movable carriage is within a threshold distance from the charging device. The wristband also includes a connector device to send the power to the computing device.

18 Claims, 2 Drawing Sheets

(51) Int. Cl.
  *H02J 50/80*    (2016.01)
  *H02J 7/02*     (2016.01)
  *H02J 50/10*    (2016.01)
  *A61B 5/00*     (2006.01)
  *A61B 5/024*    (2006.01)
  *H02J 5/00*     (2016.01)
  *A44C 5/00*     (2006.01)

(52) U.S. Cl.
  CPC ............ *H02J 50/10* (2016.02); *A44C 5/0007* (2013.01); *A61B 5/746* (2013.01); *A61B 2560/0204* (2013.01)

(56) References Cited

U.S. PATENT DOCUMENTS

| | | | | |
|---|---|---|---|---|
| 2013/0285605 | A1* | 10/2013 | Partovi | H02J 7/0042 320/108 |
| 2014/0015493 | A1  | 1/2014  | Wirz et al. | |
| 2014/0177399 | A1  | 6/2014  | Teng et al. | |
| 2014/0347799 | A1  | 11/2014 | Ono | |
| 2014/0375246 | A1  | 12/2014 | Boysen et al. | |
| 2015/0130411 | A1  | 5/2015  | Kim | |
| 2015/0189976 | A1  | 7/2015  | Lee et al. | |
| 2015/0364938 | A1* | 12/2015 | Lapetina | H01F 27/365 320/114 |
| 2016/0062319 | A1* | 3/2016  | Kim | G04C 10/00 368/204 |
| 2017/0170677 | A1* | 6/2017  | Park | H02J 7/025 |

FOREIGN PATENT DOCUMENTS

| | | |
|---|---|---|
| CN | 104824927 A    | 8/2015 |
| JP | 2004260917 A   | 9/2004 |
| JP | 2012080636 A   | 4/2012 |
| KR | 20150125214 A  | 11/2015 |
| WO | WO-2015/100396 | 7/2015 |

* cited by examiner

MOVABLE CHARGING COIL WITHIN WRISTBAND

BACKGROUND

The use of computing devices has become prevalent. For example, wearable devices allow users to wear a computing device that may perform various functions associated with how the wearable device is worn. Examples of wearable devices include step counters, smartwatches, biometric devices, and the like.

BRIEF DESCRIPTION OF THE DRAWINGS

Some examples of the present application are described with respect to the following figures.

DETAILED DESCRIPTION

As described above, the use of computing devices has become prevalent. For example, smartwatches have become popular wearable devices that provide a user with timekeeping functionality as well as other computing functionality, such as text messaging, heart rate monitoring, and the like. A smartwatch may include a rechargeable battery that may be charged by connecting the smartwatch to a power source via a cable. As such, the use of smartwatches may be limited by the battery life of the smartwatch and the availability of the power source and cable.

Examples discussed herein may provide wireless charging for a smartwatch and/or other wrist-worn devices. The smartwatch may include a movable carriage within the wristband of the smartwatch. The movable carriage may be movable within the wristband of the smartwatch and may include a charging coil that may wirelessly receive power from a charging device when the movable carriage is within a threshold distance from the charging device, allowing the smartwatch to be charged. As referred to herein, a movable carriage is any suitable device that is capable of moving within its environment and that is capable of housing a charging coil. A charging coil is any suitable coil capable of receiving power from a primary coil through induction. A charging device may be any suitable device capable of providing power to the charging coil in the smartwatch through a primary coil in the charging device. The threshold distance may be any suitable distance between the movable carriage and the charging device that allows the charging coil in the moveable carriage to receive power from the charging device.

When a user wears the smartwatch, the movable carriage of the smartwatch may move based on the user's movement. For example, when the user's hand and wrist are resting on a surface (e.g., a tabletop, a keyboard, etc.), the movable carriage may move toward the surface on which the user's hand and wrist are resting. The surface may be, or may include, the charging device, and the smartwatch may be wirelessly charged while the user's hand and wrist are resting on the surface, since the movable carriage is moved toward the surface and toward the charging device. The charging device may be any suitable surface upon which a user may rest a hand and/or wrist, thus resting the smartwatch on the surface. For example, the charging device may be a mousepad, a keyboard, a tabletop, a surface, a laptop surface, an armrest, and the like.

Figure 1:
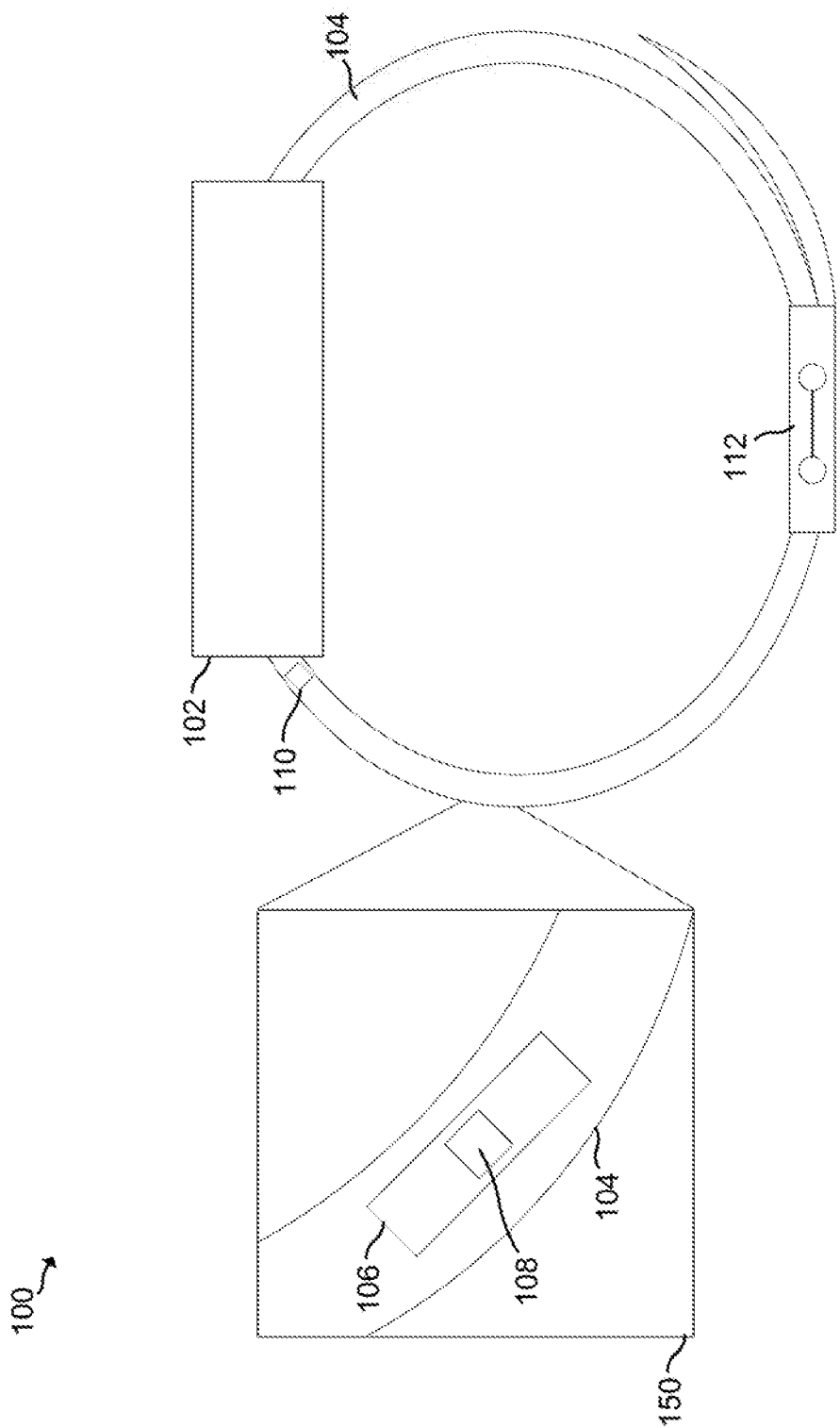
FIG. 1 illustrates an example apparatus in the form of a smartwatch having a computing device and a wristband with a movable charging coil.

Referring now to the figures, FIG. 1 illustrates an example apparatus 100 in the form of a smartwatch having a computing device 102 and a wristband 104 with a movable charging coil 108. The computing device 102 may be any suitable computing device to perform various computing functions, such as time keeping, text messaging, providing alerts and/or notifications, heart rate monitoring, providing various media (e.g., music, videos, pictures, etc.), activity tracking, providing email functionality, and the like. In some examples, the computing device 102 is a watch face capable of performing various computing functions. In some examples, the computing device 102 is any electrically-powered device.

The wristband 104 of the apparatus 100 may be coupled to the computing device 102 and may be any suitable wristband of any suitable material to secure the computing device 102 to a user's wrist or arm using the wristband securing device 112, which may be any suitable device to secure the wristband 104 to a user's wrist or arm (e.g., a clasp). The wristband 104 includes a movable carriage 106, as shown in the internal view 150 of the wristband 104.

The movable carriage 106 may be any suitable device capable of moving within the wristband 104. The movable carriage 106 may house a charging coil 108 such that the charging coil 108 may move within the wristband 104 via the movable carriage 106. The charging coil 108 may be any suitable coil to wirelessly receive power from a charging device when the movable carriage 106 is within a threshold distance from the charging device.

The moveable carriage 106 may move within the wristband 104 in any suitable manner. In some examples, the movable carriage 106 may be moved by gravity such that the movable carriage 106 may travel to the lowest point of the wristband 104. In some examples, the movable carriage 106 may include any suitable weight, such as fluid, to move the movable carriage 106 based on gravity. In some examples, the movable carriage 106 may include at least one wheel, and the movable carriage 106 may move using the wheel. In some examples, the movable carriage 106 may include a magnet, and the movable carriage 106 may be moved when the magnet is attracted to another magnet within the charging device. In some examples, the wristband 104 may be filled with a lubricating, non-conducting fluid such that the movable carriage 106 may more easily move within the wristband 104.

The wristband 104 may also include a connector device 110, which may be any suitable device to send and/or transfer power to the computing device 102 such that the computing device 102 may be charged. For example, the charging coil 108 may wirelessly receive energy from a charging device, and that energy may be converted to direct current (DC) power by a conversion circuit within the wristband 104. The conversion circuit may send the DC power to the connector device 110, which may transfer the DC power to the computing device 102 in order to charge the computing device 102.

Figure 2:
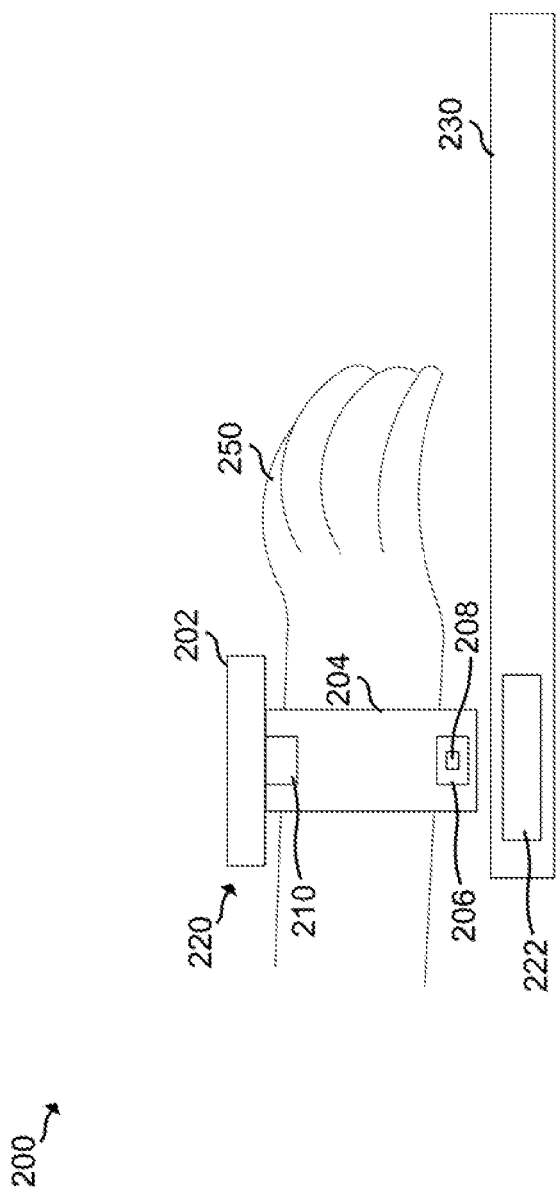
FIG. 2 illustrates an example system including a smartwatch with a movable charging coil within the wristband of the smartwatch and a charging device to charge the smartwatch.

FIG. 2 illustrates an example system 200 including a smartwatch 220 with a movable charging coil 208 within the wristband 204 of the smartwatch 220 and a charging device 230 to charge the smartwatch 220. The smartwatch 220 is similar to the apparatus 100 of FIG. 1 and includes a computing device 202 and a wristband 204 coupled to the computing device 202. The wristband 204 includes a movable carriage 206, which is similar to the movable carriage 106 of FIG. 1. The movable carriage 206 is movable within the wristband 204 and has a charging coil 208 to wirelessly receive power from the charging device 230 when the movable carriage 206 is within a threshold distance from the charging device 230. The wristband 204 also includes a connector device 210, which is similar to the connector device 110 of FIG. 1. The connector device 210 may send the wirelessly-received power to the computing device 202 in order to charge the computing device 202.

The charging device 230 may be any suitable device to wirelessly charge the smartwatch 220 using a primary coil 222 in the charging device 230 to provide power to the smartwatch 220 wirelessly. The charging device 230 may be connected to any suitable power source, such as via a USB, battery, a wall outlet, solar powered, and the like.

In some examples, the charging device 230 may be any suitable surface capable of wirelessly charging the smartwatch 220, such as a keyboard, a mousepad, a tabletop, a laptop surface, an armrest, and the like. For example, if the charging device 230 is a keyboard, the smartwatch 220 may be charged by the charging device 230 while the user types on the keyboard.

When a user wears the smartwatch 220 around the user's wrist or arm, the user may rest the user's arm, wrist, and/or hand 250 on the charging device 230, which may cause the movable carriage 204 to move downward within the wristband 204 toward the charging device 230. When the movable carriage 204 is moved to a location that is within a threshold distance from the primary coil 222 in the charging device 230, the charging coil 208 within the movable carriage 204 may wirelessly receive power from the primary coil 222 of the charging device 230. This threshold distance may be the maximum distance between the movable carriage 204 and the primary coil 222 at which the charging coil 208 is still capable of receiving power from the primary coil 222.

What is claimed is:

1. An apparatus, comprising:
   a computing device; and
   a wristband coupled to the computing device, the wristband comprising:
   a movable carriage movable inside the wristband, the movable carriage having a charging coil to wirelessly receive power from a charging device when the movable carriage is within a threshold distance from the charging device; and
   a connector device to send the wirelessly received power to the computing device.

2. The apparatus of claim 1, wherein the movable carriage is movable downward inside the wristband by gravity.

3. The apparatus of claim 1, wherein the movable carriage includes at least one wheel.

4. The apparatus of claim 1, wherein the movable carriage includes a magnet and wherein the movable carriage is moved when the magnet is attracted to another magnet within the charging device.

5. The apparatus of claim 1, wherein the movable carriage includes fluid.

6. The apparatus of claim 1, wherein the charging device is a mousepad, a keyboard, a tabletop, a surface, a laptop surface, or an armrest.

7. The apparatus of claim 1, wherein the wristband is filled with a lubricating non-conducting fluid.

8. A smartwatch, comprising:
   a watch face; and
   a wristband coupled to the watch face, the wristband comprising:
   a movable carriage movable inside the wristband to move downward inside the wristband by gravity, the movable carriage having a charging coil to wirelessly receive power from a charging device when the movable carriage is within a threshold distance from the charging device; and
   a connector device to send the wirelessly received power to the watch face.

9. The smartwatch of claim 8, wherein the movable carriage includes at least one wheel or includes fluid.

10. The smartwatch of claim 8, wherein the movable carriage includes a magnet and wherein the movable carriage is moved when the magnet is attracted to another magnet within the charging device.

11. The smartwatch of claim 8, wherein the charging device is a mousepad, a keyboard, a tabletop, a surface, a laptop surface, or an armrest.

12. The smartwatch of claim 8, wherein the wristband is filled with a lubricating non-conducting fluid.

13. A system, comprising:
    a charging device; and
    a smartwatch capable of being charged by the charging device, the smartwatch comprising:
    a computing device; and
    a wristband coupled to the computing device, the wristband comprising:
    a movable carriage movable inside the wristband, the movable carriage having a charging coil to wirelessly receive power from the charging device when the movable carriage is within a threshold distance from the charging device; and
    a connector device to send the wirelessly received power to the computing device.

14. The system of claim 13, wherein the movable carriage is movable downward inside the wristband by gravity.

15. The system of claim 13, wherein the movable carriage includes at least one wheel or includes fluid.

16. The system of claim 13, wherein the movable carriage includes a magnet and wherein the movable carriage is moved when the magnet is attracted to another magnet within the charging device.

17. The system of claim 13, wherein the charging device is a mousepad, a keyboard, a tabletop, a surface, a laptop surface, or an armrest.

18. The system of claim 13, wherein the wristband is filled with a lubricating non-conducting fluid.

* * * * *